United States Patent [19]

Kuehne

[11] 4,220,774

[45] Sep. 2, 1980

[54] VINCADIFFORMINE SYNTHESIS PROCESS

[75] Inventor: Martin E. Kuehne, Burlington, Vt.

[73] Assignee: Omnium Chimique, Brussells, Belgium

[21] Appl. No.: 954,741

[22] Filed: Oct. 26, 1978

[51] Int. Cl.$^2$ ........................................... C07D 471/08
[52] U.S. Cl. ...................................... 546/51; 546/85; 546/86; 260/583 H; 260/14; 260/15; 568/458; 568/495
[58] Field of Search ......................................... 546/51

[56] References Cited

PUBLICATIONS

Kutney et al., J.A.C.S. 90, 3891 (1968).

Primary Examiner—Donald G. Daus
Assistant Examiner—David E. Wheeler

[57] ABSTRACT

The preparation of vincadifformine and some derivatives thereof for use as a starting material for synthesis of the corresponding vincamine derivatives or for synthesis of bisindole alkaloids having clinically important antitumor properties.

10 Claims, No Drawings

VINCADIFFORMINE SYNTHESIS PROCESS

BACKGROUND OF THE INVENTION:

(1) Field of the Invention

The present invention relates to a process for the synthesis of vincadifformine and related derivatives.

(2) Description of the Prior Art

The compounds prepared by the process of the invention are of the general formula:

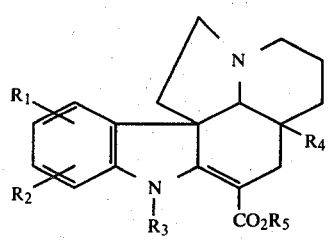

(I)

wherein:

$R_1$ and $R_2$ are the same or different and are selected from the group consisting of hydrogen, hydroxy, acyloxy, carbamate, halo, lower alkyl or alkoxy radical;

$R_3$ is hydrogen or a lower alkyl;

$R_4$ is a lower alkyl or a substituted alkyl such as an alkoxyethyl or a hydroxy substituted alkyl.

$R_5$ is a lower alkyl radical.

The term "lower alkyl", as used in this application, means saturated hydrocarbon radicals, branched or not, containing from one to seven carbon atoms.

The numbering of vincadifformine and its derivatives is in accordance with the teachings of Le Men and Taylor, Experientia 1965, 21, 508.

Vincadifformine of the formula Ia ($R_1=R_2=R_3=H$, $R_4=$ethyl, $R_5=$methyl) is an alkaloid which is the raw material used in the preparation of the vincamine group alkaloids as described in Belgian Pat. No. 772,005 and Belgian Pat. No. 848,475.

Vincamine and some vincamine derivatives are well-known alkaloids used in human therapeutics as psychotropic drugs having high efficiency and having a relatively low order of toxicity. Furthermore, it has been shown that the rearrangement of vincadifformine resulting in vincamine may be applied to a large number of vincadifformine derivatives to provide vincamine related compounds (see French Patent Application No. 76 22336, French Patent Application No. 76 22275 and Belgian Pat. No. 816,692).

Vincadifformine derivatives may also be used as a starting material for the synthesis of therapeutically useful bisindole alkaloids. Vincadifformine of the formula $I_b$ ($R_1=11$ methoxy, $R_2=R_3=H$, $R_4=$ethyl and $R_5=$methyl) may be easily N(a)-methylated to provide a compound which may be used as the starting material for synthesis of the vindoline moiety of the anti-tumor agent vinblastine (J. P. Kutney et al., J. Amer. Chem. Soc. 100, 4220, 1978).

Two vincadifformine synthesis methods are disclosed in the literature: Kutney et al., J. Amer. Chem. Soc. 90, 3891, 1968 and J. V. Laronze et al., Tetrahedron Letters 491, 1974. A further method of total synthesis of vincadifformine is disclosed in applicant's U.S. Patent application Ser. No. 865,657 filed on Dec. 29, 1977 now U.S. Pat. No. 4,154,943.

11-methoxy vincadifformine (ervinceine) of the formula Ib is an alkaloid occurring in Vinca Erecta and described by D. A. Rakhimov, V. M. Malikov, M. R. Yagudaev and S. N. Yunusov (Khim. prir. Soedin. 226, 1970).

It is one object of the present invention to provide a method of synthesizing vincadifformine and related polycyclic compounds, the method producing high yields, the method having a reduced number of intermediate steps, and the method using inexpensive reagents.

SUMMARY OF THE INVENTION

In accordance with the synthesis process of the present invention, an α-carboalkoxy-α-methyl-tetrahydro-β-carboline compound and an aldehyde are condensed in one step to provide the corresponding vincadifformine. The synthesis process has a high yield, has a reduced number of steps and uses inexpensive reagents.

DETAILED DESCRIPTION OF THE INVENTION

The starting raw material used is an α-carbomethoxy-α-methyl-tetrahydro-β-carboline of the following general formula:

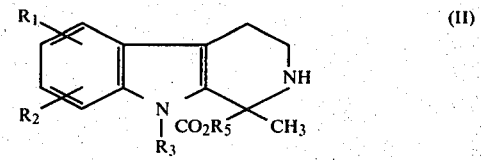

(II)

wherein $R_1$, $R_2$, $R_3$ and $R_5$ have the meaning previously described. These compounds can be advantageously obtained by condensing the corresponding tryptamine with an alkyl pyruvate. The following is an example of such a reaction:

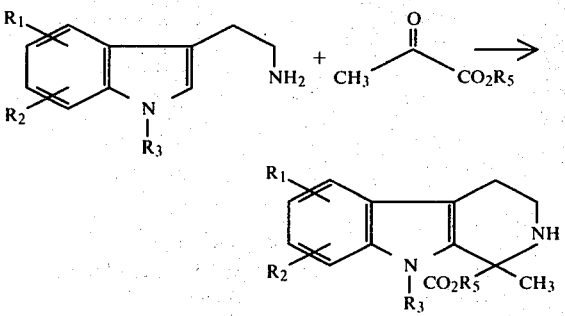

According to the present invention, compound (II) is condensed with an appropriate functionalized aldehyde to yield vincadifformine or a vincadifformine derivative. The aldehyde is of the following general formula:

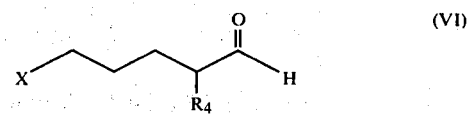

(VI)

The aldehyde is preferably a 2-alkyl substituted 5-halo, arylsulfoxy, alkyl or fluoroalkylsulfoxy-pentanal for which a corresponding tertiary enamine may be N-alkylated intramolecularly. Examples of such aldehydes are 5-chloro-2-ethylpentanal, 5-bromo-2-ethylpentanal, 5-sulfomethoxy-2-ethylpentanal.

As shown in the schedule which follows, the preferred aldehyde is 5-chloro-2-ethylpentanal (VIa) and is preferably prepared by condensing a primary amine such as cyclohexylamine (III) with butyraldehyde (IV) to form 1-butylidine cyclohexylamine (V). 1-butylidine cyclohexylamine (V) on reaction with a strong base such as lithium diisopropylamine and alkylation with 1-bromo-3-chloropropane gives the 5-chloro-pentanal (VIa).

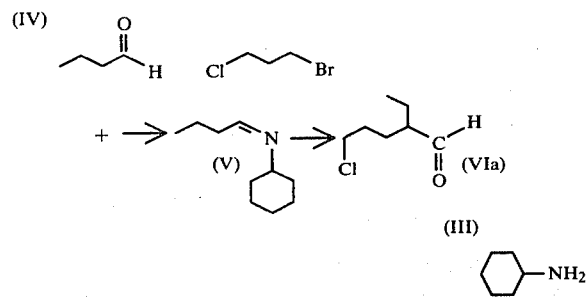

The condensation occurs by heating compound II and one to two molar equivalents of aldehyde VI in a suitable solvent and in presence of a small amount of acid catalyst for 10 to 160 hours. It is preferable to use an aromatic solvent such as dry benzene or toluene, but, other inert solvents may be used. It has been found that p-toluene sulfonic acid is a suitable acid catalyst. Water formed during the initial enamine formation is preferably eliminated from the reaction mixture by using a Dean-Stark water separator or molecular sieves. The temperature of the reaction medium may vary from about 30° C. to the boiling point of the reaction mixture, but, the temperature of the reaction medium is advantageously about 100° C.

In some cases, that is, for vincadifformine synthesis, after an initial period of heating in presence of the acid catalyst, an organic base such as diazabicycloundecene (DBU) may be advantageously added.

The condensation products are isolated from the reaction mixture in accordance with the standard procedures of the art.

The following examples describe the synthesis method of the invention.

EXAMPLE 1: PREPARATION OF 1-BUTYLIDENE CYCLOHEXYLAMINE (FORMULA V)

At 0° C., 16.3 g (20 mL, 0.23 mol) of butyraldehyde (Formula IV) was added dropwise to 21.7 g (25 mL, 0.22 mol) of cyclohexylamine (Formula III). After 1 h, 6 g of anhydrous sodium sulfate was added and the mixture stirred for 5 h. The product was decanted from the salt water slurry, dried by addition of further 10 g of anhydrous sodium sulfate, filtered and distilled. Characteristics of the product: bp 88° C. (20 mm); yield 86%; NMR (CDCl$_3$, δ): 1.0 (3H, t) 1.1–2.1 (12H), 2.3 (2H, g), 3.0 (1H, m), 7.8 (1H, t).

EXAMPLE 2: PREPARATION OF 5-CHLORO-2-ETHYL PENTANAL (FORMULA VIa)

A solution of 15.3 g (18.2 ml, 0.10 mol) of 1-butylidene cyclohexylamine (Formula V) in 30 mL of tetrahydrofuran was added at −78° C. to a solution of lithium diisopropylamide (0.105 mol), prepared from 45.6 ml of 2.3 molar n-butyllithium and 16 ml of diisopropylamine in 20 ml of tetrahydrofuran under nitrogen. After 30 min 11 ml (0.11 mol) of 1-bromo-3-chloropropane was added dropwise at −78° C. over 30 min. The reaction mixture was allowed to warm to 20° C. and stirred for 48 h. Addition of 200 ml of water and extraction with two 150 ml portions of dichloromethane, washing of the extracts with 200 ml of brine, and concentration gave a yellow oil which was combined with 40 g of oxalic acid in 350 ml of water. Steam distillation and subsequent redistillation provided 5.5 g (37% yield) of the chloroaldehyde having the following characteristics: bp 43°–53° C. (50–120μ); NMR (CDCl$_3$, δ): 9.6 (1H, d), 3.5 (2H, t), 2.2 (1H, m), 1.8 (6H, m), 0.95 (3H, t).

EXAMPLE 3: PREPARATION OF A-CARBOMETHOXY-A-METHYLTETRAHYDRO-β-CARBOLINE (FORMULA II)

A solution of 4.0 g (20 m mol) of tryptamine hydrochloride and 20.0 ml (22 m mol) of methyl pyruvate in 80 ml of dry methanol was refluxed for 21 h, cooled and concentrated under vacuum. The residual solid was dissolved in 40 ml of hot water, filtered and 3 ml of conc. ammonium hydroxide solution added. The precipitated crystalline product was recrystallized from ethanol and water (3:5), giving 3.5 g (72% yield) and had the following characteristics: mp 136°–138° C. (reported mp 138° C.*); NMR (CDCl$_3$, δ): 8.6 (1H, s), 7.3–7.9 (4H, m), 3.9 (3H, s), 3.3 (2H, t), 2.8 (2H, sp.t).
* G. Hahn, D. Scheles, L. Buerwald and H. Werner, Just. Lieb. Ann., 520, 107 (1935).

EXAMPLE 4: PREPARATION OF VINCADIFFORMINE (FORMULA I)

A solution of 300 mg (1.23 m mol) of a-Carbomethoxy-a-methyltetrahydro-β-carboline (Formula II) and 0.22 ml (1.5 m mol) of 5-chloro-2-ethyl-pentanal and 1 mg of p-toluenesulfonic acid in 25 ml of toluene was refluxed 100 h under nitrogen with a Dean Stark water separator. To the hot solution 0.38 ml (3.0 m mol) of diazabicycloundecene (DBU) was added and heating continued for 18 h. The reaction mixture was cooled, concentrated under vacuum and the residue dissolved in dichloromethane. Filtration through a column of Baker silica (25 g, 40 cm length) and washing with 3% methanol in dichloromethane gave 360 mg (84%) of crude vincadifformine after concentration under vacuum of the second 100 ml of eluate. The NMR spectrum of this product matched that of an authentic sample of dl-vincadifformine and TLC comparison indicated only minor impurities. Recrystallization from acetonitrile gave a sample, mp and mixture mp 124°–125° C. (reported 124°–125° C.*). MS (80 eV) m/e (rel. intens. %): 124 (100), 214 (4), 328 (85) M+.
* C. Djerassi, H. Budzikiewicz, J. M. Wilson, J. Gosset, M. M. Janot, Tet. Lett. 235 (1962); J. Gosset, J. LeMen, M. M. Janot, Ann. Pharm. France, 20, 448 (1962).

EXAMPLE 5: PREPARATION OF 1-CARBOMETHOXY-7-METHOXY-1-METHYL-1,2,3,4-TETRAHYDRO-9H-PYRIDO[3,4-B]INDOLE (IIB)

A solution of 113 mg of 6-methoxytryptamine[1] and 80 μL of methyl pyruvate in 5 mL of methanol was refluxed under nitrogen for 18 h. The cooled reaction mixture was partitioned between 10 mL of saturated aqueous sodium carbonate and 15 ml of dichloromethane and the aqueous phase extracted with two 15 ml portions of dichloromethane. The combined organic extracts were washed with brine, filtered through phase separating paper and concentrated. Trituration with 2 mL of ether gave 110 mg (80% yield) of product with mp 182°–184° C. An analytical sample was recrystallized from ethyl acetate to mp 184°–185° C. NMR (CDCl$_3$)δ 8.25 (br s, 1H), 7.44 (d, 1H), 6.85 (m, 2H), 3.84 (s, 3H), 3.80 (s, 3H), 3.21 (t, 2H), 2.72 (t, 2H), 2.28 (br s, 1H), 1.70 (s, 3H). Anal. Calcd. for $C_{15}H_{18}N_2O_3$: C, 65.67; H, 6.61; N, 10.21. Found: 65.68; H, 6.76; N, 9.92.

(1) R. B. Woodward, F. E. Bader, H. Bickel, A. J. Frey and R. W. Kierstead, Tetrahedron 2, 1 (1958).

EXAMPLE 6: PREPARATION OF ±ERVINCEINE (16-METHOXYVINCADIFFORMINE)

To 130 mg (0.47 mM) of the methoxytetrahydrocarboline ester IIb and a crystal of p-toluene sulfonic acid in 3 ml of toluene was added 100 μl (0.75 mM) of 5-chloro-2-ethylpentanal in 1 ml of toluene. Under a Dean-Stark water trap containing 3 Å Davison Molecular Sieves and a nitrogen atmosphere, the mixture was refluxed for 72 h. Concentration and partitioning of the residue between 10 ml of 10% HCl and 5 ml of hexane, addition of excess KOH to the aqueous solution followed by four extractions with 15 ml of dichloromethane and concentration gave a basic residue. This was purified by solution in 50 ml of ethyl acetate and rapid filtration of the solution through 3 g of Baker silica gel. The concentrated eluate gave 160 mg (92%) of ervinceine as an amber oil which was homogeneous by TLC (Merck Silica gel, Rf 0.7, ethyl acetate). The product formed a picrate, mp and mmp 183°–184° C., and had spectroscopic data matching those of an authentic sample. NMR (CDCl$_3$)δ 8.90 (br s, 1H), 7.00–7.28 (m, 1H), 6.30–6.50 (m, 2H), 3.76 (s, 6H), 3.40–0.80 (m, 15H), 0.58 (t, 3H); MS (80eV) m/e (rel intens. %): 124 (100), 184 (12), 244(12), 309(12), 368 (90) M+.

EXAMPLE 7: PREPARATION OF N(A)-METHYLTRYPTAMINE

A solution of 3.20 g (20.0 m mol) of tryptamine and 3.10 g (20.0 m mol) of phthalic anhydride in 40 ml of toluene was refluxed under a Dean-Stark water separator for 12 h. Cooling, filtration and concentration of the filtrate gave a crude phthalimide which was recrystallized from ethanol to produce 4.85 g (84%), of phthalimide, mp 164°–165° C.; reported 164°–165° C.[3]

A solution of 0.58 g (2.0 m mol) of the phthalimide in 1.5 mL of dimethylformamide (DMF) was added over 2 min to (0.22 m mol) of 50% sodium hydride in mineral oil suspended in 1 mL of DMF. After stirring at 20° C. under $N_2$ for 30 min, 0.25 ml (4.0 m mol) of methyliodide was added. The dark brown solution turned pale yellow. After 15 min the mixture was poured into 40 ml of half saturated brine and the resultant precipitate was filtered after 20 min and washed with water. Recrystallization of the N-methyl derivative from ethanol gave 0.40 g (65%) mp 174°–175° C., reported 175°–176° or 177°–178° C.[4,5]

A mixture of 824 mg (2.7 m mol) of the N-methyl tryptamine phthalimide and 0.7 ml (14 m mol) of hydrazine hydrate (85% solution, Fischer) in 80 ml of ethanol was refluxed for 24 h; then 20 ml of 10% aqueous HCl was added and the solution refluxed an additional 30 min. After cooling, concentration and partitioning of the residue beween 60 mL of saturated aqueous sodium carbonate and 60 ml of dichloromethane, the aqueous portion was extracted with 60 ml of dichloromethane and the combined organic extracts were washed with brine. Concentration and Kugelrohr distillation gave 0.45 g (96%); bp 95°–105° C. (0.06 mm). The oil was dissolved in ethyl acetate and HCl gas bubbled into the solution. The resultant amine hydrochloride was filtered and washed with ethyl acetate containing HCl and then with ether. The N(a)-methyl tryptamine hydrochloride had a mp 201°–202° C.; reported 198°–199° C.[6,7]

(3) R. H. F. Manske, J. Am. Chem. Soc., 51, 1202 (1929).
(4) S. Sugasawa and M. Murayama, Chem. Pharm. Bull., 6, 194 (1958).
(5) T. Hino, ibid, 9, 988 (1961).
(6) H. Wieland, W. Kung, and H. Mittasch, Justus Liebigs Ann. Chem., 613, 1 (1939).
(7) A. W. Jackson and A. E. Smith, J. Chem. Soc., Suppl. 5510 (1964).

EXAMPLE 8: PREPARATION OF 1-CARBOMETHOXY-1-METHYL-1,2,3,4-TETRAHYDRO-9-METHYL-PYRIDO[3,4-B]LINDOLE (IIC).

A mixture of 160 mg of N(a)-methyltryptamine hydrochloride and 0.1 ml (ca. 50% excess) of methylpyruvate in 5 ml of methanol was refluxed under nitrogen for 30 h. The cooled solution was concentrated under vacuum and the residue partitioned between 20 ml of 10% aq. HCl and 10 ml of hexane. The aqueous layer was made basic with KOH and extracted with three 20 ml portions of dichloromethane. The extracts were washed with brine, concentrated to dryness and the residue, dissolved in ethyl acetate, passed through 4 g of Baker silica gel. Concentration and Kugelrohr distillation (bp 150°–160° C., 0.03 mm) gave 158 mg (80%) of the tetrahydro-β-carboline. NMR (CDCl$_3$)δ 7.3(m, 4H), 3.77(s, 3H), 3.70 (s, 3H), 3.18(t, 2H), 2.78(t, 2H), 2.22(br s, 1H) 1.75 (s,3H). Anal. Calcd for $C_{15}H_{18}N_2O_2$: C, 69.74; H, 7.02; N, 10.85. Found: C, 69.50; H, 6.94; N, 10.63. A picrate recrystallized from ethanol had mp 190°–191° C.

EXAMPLE 9: PREPARATION OF MINOVINE (IIIC)

The preparation followed the procedure given for ervinceine. Starting with 129 mg of the β-carboline (Formula IIc) and using 50 mL of ether in place of ethyl acetate in the filtration through 2 g of silica gel gave 140 mg of crude product which showed two components by TLC[Rf 0.2 and 0.7, major (minovine), ethyl acetate, silica gel]. Preparative TLC gave 65 mg (37%) of minovine as an oil with an NMR spectrum identical with that of sample obtained by methylation of ±vincadifformine. The synthetic sample crystallized slowly from 10:1 hexane-ether and had mp and mixture mp 119°–121° C. A picrate was recrystallized from methanol-ether, mp and mmp 194°–197° C. The contaminant with Rf 0.2 was found to arise from minovine on storage. In subsequent experiments minovine was obtained by the same procedure in 56% yield without preparative TLC.

A solution of 34 mg (0.1 m mol) of ±vincadifformine in 1 ml of DMF was added at 20° C. to a mixture of 10 mg (0.2 m mol) of 50% NaH-mineral oil in 1 ml of DMF. After 20 min 20 μL (0.3 m mol) of methyl iodide was added to the brown solution. After 10 min 5 ml of water was added resulting in deposition of a gummy product. Decantation of the solvent, addition of ether, filtration of the ether solution through phase separating paper and concentration under vacuum gave 30 mg (85%) of minovine which showed no indolic NH singlet at δ 8.9 and the presence of the N-CH$_3$ singlet at 3.24, integrating for 3 protons. A picrate was prepared with mp 194°–197° C., regeneration of the free base gave minovine, mp 119°–121° C., reported 120°–122° C.[8] MS (80eV) m/e (vel. intensity %): 124 (100), 168 (7), 228 (4) 267 (7), 352 (55) M+.

(8) J. Mokry, I. Kompis, L. Dubavkova and P. Sefcovic, Experientia, 19, 311 (1963).

What I claim is:

1. A process for the preparation of vincadifformine and substituted vincadifformines of the formula:

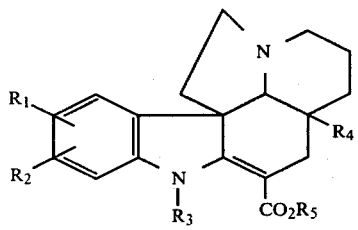

wherein:

$R_1$ and $R_2$ are the same or different and are selected from the group consisting of hydrogen, hydroxy, lower alkanoyloxy, lower alkyl carbamoyloxy, halo, lower alkyl and alkoxy groups;

$R_3$ is hydrogen or a lower alkyl group;

$R_4$ is a lower alkyl, lower hydroxyalkyl or lower alkoxyalkyl group;

$R_5$ is a lower alkyl group;

the process comprising the step of condensing a carboline derivative of the formula

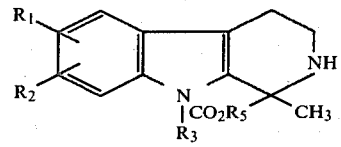

wherein $R_1$, $R_2$, $R_3$, and $R_5$ have the aforementioned meanings, with an aldehyde of the formula

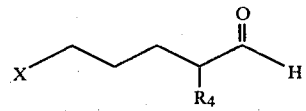

wherein X is a good leaving group selected from the group consisting of halo, benzene sulfoxy, P-toluenesulfoxy, lower alkyl or fluoralkylsulfoxy groups and $R_4$ has the same meaning as described above, this condensation being effected in a solvent inert to the reaction conditions and at a temperature in the range of 30° C. to the boiling point of the solvent.

2. The process of claim 1 wherein said aldehyde is 5-chloro-2-ethylpentanal.

3. The process of claim 1 wherein the condensation is effected in presence of an acid.

4. The process of claim 3 wherein the acid is p-toluene sulfonic acid.

5. The process of claim 1 wherein the condensation is effected in two stages, the first stage being heating the reaction mixture in the presence of an acid catalyst and the second stage being adding a non-nucleophilic base and further heating the reaction mixture.

6. The process of claim 5 wherein the base is diazabicycloundecene.

7. The process of claim 1 wherein the condensation is effected in benzene.

8. The process of claim 1 wherein the condensation is effected in toluene.

9. The process of claim 1 wherein the temperature is approximately 100° C.

10. The process of claim 4 wherein the temperature is approximately 100° C.